United States Patent [19]

Schildknecht et al.

[11] Patent Number: 5,258,373
[45] Date of Patent: *Nov. 2, 1993

[54] ANTICOCCIDIAL COMPOSITIONS

[75] Inventors: Eugene G. Schildknecht, Hackettstown; Govind G. Untawale, Wayne, both of N.J.

[73] Assignee: Hoffmann-La Roche Inc., Nutley, N.J.

[ * ] Notice: The portion of the term of this patent subsequent to Feb. 26, 2008 has been disclaimed.

[21] Appl. No.: 731,682

[22] Filed: Jul. 17, 1991

[51] Int. Cl.$^5$ ............... A61K 31/655; A61K 31/505; A61K 31/35; A61K 35/00
[52] U.S. Cl. .................................. 514/157; 514/275; 514/453; 424/114
[58] Field of Search ............... 514/272, 275, 453, 157, 514/158; 424/115, 114

[56] References Cited

U.S. PATENT DOCUMENTS

| 3,461,206 | 8/1969 | Hoffer et al. | 514/275 |
| 4,839,382 | 7/1989 | Maestrone et al. | 514/453 |
| 4,996,198 | 2/1991 | Schildknecht et al. | 514/157 |

*Primary Examiner*—Frederick E. Waddell
*Assistant Examiner*—K. Weddington
*Attorney, Agent, or Firm*—George M. Gould; George W. Johnston; Alan P. Kass

[57] ABSTRACT

Compositions comprising a mixture of the antibiotic frenolicin B with a potentiated sulfonamide anticoccidial agent, useful for the treatment and prevention of coccidiosis in animals and methods of treating coccidiosis are disclosed.

5 Claims, No Drawings

ANTICOCCIDIAL COMPOSITIONS

BACKGROUND OF THE INVENTION

The invention relates to the field of compositions useful for the prevention and treatment of coccidiosis in animals, methods of using such compositions and animal comestibles containing such compositions.

Coccidiosis is a disease caused by microscopic protozoal parasites called coccidia, belonging to the genus Eimeria. The infection in the host animals is initiated by the ingestion, usually along with food, water, and/or fecal material, of Eimeria organisms in the sporulated oocyst stage. When the ingested oocysts enter the intestine, the infectious stage of the Eimeria soon develops from the oocysts and causes extensive damage to the inner walls of the intestine and the cecum or "intestinal pouch." Cecal coccidiosis in chickens, for example, is caused primarily by the organism *E. tenella* and results in the destruction of the cecal linings of the host.

A number of coccidiostatic agents are presently available for the prevention and/or treatment of coccidiosis. Still, many of these agents have certain shortcomings. Animals treated with some of the known coccidiostats sometimes show reduced feed efficiency and lower weight gains than normal. Moreover, the development of resistance to the more commonly used agents is becoming an increasingly significant problem; one which is becoming a limiting factor in successfully combating coccidiosis. Still other agents have very narrow safety and efficacy ranges with resulting toxicity risks for treated animals, as well as for other farm animals and man by virtue of incidental or accidental exposure or ingestion.

A napthoquinone antibiotic produced from *Streptomyces roseofulvus*, frenolicin B, has been shown to have some anticoccidial activity against *E. tenella* in chickens (Omura, et al., *J. Antibiotics*, Vol. 38, No. 10, pp. 1447-8 (1985)). Frenolicin B has recently been shown to be synergistic in combination with ionophoric anticoccidial antibiotics against which Eimeria field isolates had developed resistance due to the chronic usage of these agents to combat coccidiosis. See U.S. Pat. No. 4,839,382.

SUMMARY OF THE INVENTION

It has now been discovered that compositions that contain a combination of frenolicin B and potentiated sulfonamide anticoccidials result in significantly potentiated activity against coccidiosis caused by Eimeria that have developed resistance to these anticoccidials. The activity of the instant compositions is greater than would be expected from a simple additive effect of the two components.

DETAILED DESCRIPTION OF THE INVENTION

The present invention is directed to compositions which are useful for the prevention and treatment of coccidiosis in animals comprising a mixture of frenolicin B and potentiated sulfonamide anticoccidial agents such as sulfadimethoxine plus ormetoprim.

These compositions are especially useful by virtue of their potentiated activity against strains of Eimeria which have become resistant to the aforementioned chemical anticoccidials which have been approved for and used in the treatment of coccidiosis especially in poultry.

The compositions of the present invention, when administered to animals such as domestic animals and animals raised commercially for food such as poultry, cattle, sheep and pigs, are effective in the prophylaxis and treatment of coccidiosis. The frenolicin B synergistically interacts with the sulfonamide component of the instant composition resulting in greater activity against resistant coccidiosis. Another advantage of the present invention is that the use of the frenolicin makes possible the use of reduced amounts of the active ingredients with resulting reduction in the risk of toxicity and the side effects typically associated therewith such as adverse influence on feeding, water intake, and nutrient absorption.

The production and isolation from *Streptomyces roseofulvus* of the frenolicin B utilized in the present invention is disclosed in the article by Iwai et al., *J. Antibiotics*, Vol. 31 no. 10, pp. 959-965 (1978).

The sulfonamides are a known class of antibiotics which are characterized by the radical $SO_2NH_2$. Suitable sulfonamides for these compositions are any of those that when combined with the described potentiator are useful in combating coccidiosis in animals, including the sulfonamides described in U.S. Pat. No. 3,461,206.

Preferred for use in the practice of this invention is sulfadimethoxine.

These sulfonamides are employed in the present compositions in conjunction with a potentiator of their activity, namely a substituted pyrimidine potentiator, and more specifically a 2,4-diamino-5-(trisubstituted)benzyl-pyrimidine sulfonamide potentiator of the formula:

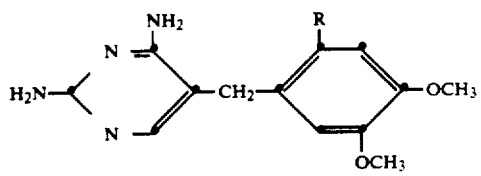

in which R is methoxy, methyl or ethyl.

Exemplary of suitable compounds within the above formula which are useful in the present compositions as potentiators for the sulfonamide are the following:

2,4-diamino-5-(2',4',5'-trimethoxybenzyl)pyrimidine(-trimethoprim)

2,4-diamino-5-(2,methyl-4',5'-dimethoxybenzyl)-pyrimidine (ormetoprim)

2,4-diamino-5-(2'-ethyl-4,5'-dimethoxybenzyl)pyrimidine

Especially preferred for use in the present composition are combination of sulfadimethoxine and ormetoprim.

The 2,4-diamino-5-(trisubstituted)benzyl-pyrimidine potentiator is generally employed in these compositions in amounts ranging from about 0.01 to about 20 parts by weights for each part by weight of the sulfonamide. More effectively, however, the weight ratio of the sulfonamide to the 2,4-diamino-5(trisubstituted)benzyl pyrimidine in the compositions is in the range from about 20:1 to about 1:1, with especially efficacious results being obtained using weight ratios of about 5:3 or about 5:1 (about 5:3 being the most favored).

The individual components of the compositions of the present invention are employed in relative amounts which are synergistic in combating coccidiosis-producing microorganisms and in particular against those strains which have developed resistance to the sulfonamide anticoccidials due to exposure over time to the latter.

The improved anticoccidial animal comestible compositions of this invention are prepared by mixing the active ingredient with suitable carrier or diluent material generally used in animal feeds or drinking water.

The concentration of the active ingredient in an animal feed composition of this invention can be adjusted to meet particular needs and may vary over a wide range. The limiting criteria of the concentration are that the minimum concentration is such that a sufficient amount of the active ingredients is provided to effect the desired control of coccidiosis and the maximum concentration is such that the amount of composition ingested does not result in any untoward or undesirable side effects. This may, of course, vary according to the potency and usual recommended dosing level for the selected coccidial agent. Furthermore, because of the potentiating interaction of the active ingredients of the present invention, the amounts of each component required, may usefully be less than that which would ordinarily be considered the usual recommended dosing level for the individual components if used separately as a coccidiostat. The amount of the sulfonamide necessary for successfully combatting coccidiosis may therefor be beneficially reduced. Thus, the potentiated sulfonamide component is typically present in an amount of from about 25 to about 90%, and preferably 33% to 75% of the normal recommended dosing level for that ionophore. For example, the approved recommended dosing level for sulfadimethoxine and ormethoprim in chicken for the prevention of coccidiosis would be about 200 ppm (125 ppm of sulfadimethoxine and 75 ppm of ormethoprim). However, the compositions in accordance with the present invention preferably contain the sulfadimethoxine/ormethoprim in an amount of from 75 to 150 ppm and the frenolicin B is present in amounts from 33 to 75 ppm.

The easiest way to administer the anticoccidials is by mixing them in the animal's feed. However, the anticoccidials can be usefully administered in other ways. For example, they can be incorporated into tablets, drenches, boluses, or capsules, and dosed to the animals. Formulations of the antibiotic compounds in such dosage forms can be accomplished by means of methods well-known in the veterinary pharmaceutical art. Of course, whatever the method or methods of administration, the two components of the composition of the present invention can be introduced independently so long as the synergistically effective combination is ultimately dosed to the animal.

The most practical way to treat animals with the anticoccidial compounds is by the formulation of the compounds into the feed or drinking water. Any type of feed may be medicated with the anticoccidial compounds, including common dry feeds, liquid feeds and pelleted feeds.

The methods of formulating drugs into animal feeds are well-known. It is usual to make a concentrated drug premix as a raw material for medicated feeds. For example, typical drug premixes may contain from about 2.0 to about 150 grams of drug per pound of premix. The wide range results from the wide range of concentration of drug which may be desired in the final feed. Premixes may be either in liquid or dry formulations. Separately formulated premixes for each of the two components could be added to a given feed lot to provide the composition of the present invention in the final medicated feed.

The formulation of animal feeds containing the proper amounts of anticoccidial for useful treatment is well understood. It is necessary only to calculate the amount of compound which it is desired to administer to each animal, to take into account the amount of feed per day which the animal eats and the concentration of antibiotic compound in the premix to be used, and calculate the proper concentration of anticoccidial compound or of premix, in the feed.

The known methods of formulating, mixing and processing feeds which are normally used in the animal feed arts are entirely appropriate for manufacturing feeds containing the anticoccidial compositions of the present invention. The compositions of the present invention are typically effective in combating coccidiosis when administered to animals in feed mixes containing the compositions in a concentration of from about 100 ppm to about 250 ppm.

The following example is illustrative of the invention.

EXAMPLE

Anticoccidial Activity Against Sulfadimethoxine/Ormetoprim

Resistant Field Strain of *E. tenella*

Experimental Procedure

Two-week old Arbor Acres, Peterson Cross broiler chickens, obtained from a commercial hatchery and kept in wire-floored, electrically heated, battery brooders, were used in all studies. Male birds, selected according to weight, were used in each group. The chickens were medicated two days before infection and maintained on the medicated feed until the termination of the trial for a total medication period of nine days. There were two replicates of eight birds each per treatment.

Eimeria Field Isolates

The *E. tenella* field isolate was recovered from a commerical broiler operation in North Carolina and forwarded to ASR. The intestinal samples were homogenized with a Waring Blender, suspended in 2.5% potassium dichromate solution, sporulated at room temperature, and inoculated into young susceptible, coccidia-free chicks for further oocyst collection and species identification.

At appropriate post-infection times, 5 to 7 days, the birds were sacrificed, autopsied, and diagnosis of Eimeria species made, based on location site, and oocysts measurement. Oocysts were collected from the intestines of the passaged birds and sporulated.

In evaluating the efficacy of the fremolicin-B combinations, $3.0 \times 10^5$ sporulated oocysts were administered per bird. The sporulated oocysts, properly agitated and suspended in sterile distilled water, were inoculated in volumes of 1.0 ml directly into the chick crop by means of a blunt needle attached to a calibrated syringe.

Criteria for Evaluating Anticoccidial Efficacy

At termination of the trials, the surviving birds were sacrificed, necropsied and scored for gross lesions. All birds that died during the experiments were also necropsied; proper diagnosis was made, and their gross lesions scored and recorded. The intestinal lesions were scored as $0=$normal, $1=$slight, $2=$moderate, $3=$severe and $4=$dead. The readings obtained were summarized as average degree of infection (ADI).

In addition, bird group weight, feed intake, feed conversion and mortality records were kept.

Results

The results are set forth in Table 1 below:

TABLE 1

Anticoccidial Activity of Frenolicin-B in Combination with Sulfadimethoxine/ormetoprim (5:3) against *Eimeria tenella*

| Treatment | Level (ppm) | Weight Gain. % | Feed Conv. | Lesion Score | % Mortality |
|---|---|---|---|---|---|
| UUC | 0 | 100 | 1.60 | 0.0 | 0 |
| IUC | — | 74 | 2.36 | 2.7 | 18.75 |
| Frenolicin B | 80 | 89 | 1.80 | 1.0 | 0 |
| Frenolicin B | 40 | 89 | 1.95 | 1.6 | 0 |
| Sulfadimethoxine/ ormetoprim (5:3) | 200 | 86 | 1.76 | 1.6 | 0 |
| Sulfadimethoxine/ ormetoprim (5:3) | 100 | 63 | 3.31 | 3.0 | 25.0 |
| Sulfadimethoxine/ ormetoprim (5:3) + Frenolicin-B | 200 + 80 | 99 | 1.80 | 0.2 | 0 |
| Sulfadimethoxine/ ormetoprim (5:3) + Frenolicin-B | 200 + 40 | 98 | 1.59 | 0.5 | 0 |
| Sulfadimethoxine/ ormetoprim (5:3) + Frenolicin-B | 100 + 80 | 96 | 1.71 | 0.8 | 0 |
| Sulfadimethoxine/ ormetoprim (5:3) + Frenolicin-B | 100 + 40 | 94 | 1.97 | 1.0 | 0 |

We claim:

1. A composition for combating coccidiosis in animals which comprises sulfadimethoxine, ormetoprim and frenolicin-B, wherein these ingredients are present in amounts which in combination are synergistically effective in combating at least one coccidiosis-causing strain of Elmeria.

2. A comestible for feeding to animals, which comprises an animal feed containing an anticoccidial composition comprising sulfadimethoxine, ormetoprim and frenolicin-B, wherein the combination of sulfadimethoxine and ormetoprim is present in an amount from about 75 to about 150 ppm by weight of the animal feed and the frenolicin-B is present in an amount which combined with the sulfadimethoxine and ormetoprim is synergistically effective in combating at least one coccidiosis-causing strain of Elmeria.

3. The comestible according to claim 2 wherein the amount of frenolicin-B is from about 33 to about 75 ppm by weight of the animal feed.

4. An animal feed additive premix containing an anticoccidial composition comprising sulfadimethoxine, ormetoprim and frenolicin-B wherein said composition is present in an amount sufficient to provide from about 100 to about 250 ppm of said composition in said animal feed.

5. A method of combating coccidiosis in animals, comprising orally administering to said animals a prophylactic or therapeutic amount of an anticoccidial composition comprising sulfadimethoxine, ormetoprim and frenolicin-B in amounts which in combination are synergistically effective in combating at least one coccidiosis-causing strain of Elmeria.

* * * * *

UNITED STATES PATENT AND TRADEMARK OFFICE
CERTIFICATE OF CORRECTION

PATENT NO. : 5,258,373
DATED : November 2, 1993
INVENTOR(S) : Eugene G. Schildknecht and Govind G. Untawale It is certified that error appears in the above-identified patent and that said Letters Patent is hereby corrected as shown below:

Column 6, line 6, change "Elmeria" to -- Eimeria --;

Column 6, line 16, change "Elmeria" to -- Eimeria --;

Column 6, line 32, change "Elmeria" to -- Eimeria --.

Signed and Sealed this

Sixteenth Day of May, 1995

*Attest:*

BRUCE LEHMAN

*Attesting Officer*     *Commissioner of Patents and Trademarks*